United States Patent [19]

Dunbar et al.

[11] Patent Number: 4,689,348
[45] Date of Patent: * Aug. 25, 1987

[54] CYANOGUANIDINES USEFUL AS ANIMAL GROWTH PROMOTING AGENTS

[75] Inventors: Joseph E. Dunbar, Midland, Mich.; Kimiaki Maruyama, Hastings, Nebr.

[73] Assignee: Dow Chemical Company, Midland, Mich.

[*] Notice: The portion of the term of this patent subsequent to Apr. 28, 2004 has been disclaimed.

[21] Appl. No.: 641,810

[22] Filed: Aug. 17, 1984

[51] Int. Cl.⁴ .................... A61K 31/17; C07C 129/14
[52] U.S. Cl. .................... 514/609; 564/104; 558/4
[58] Field of Search .................... 564/104; 424/322; 514/609

[56] References Cited

U.S. PATENT DOCUMENTS

| | | | |
|---|---|---|---|
| 3,248,426 | 4/1966 | Dvornik | 260/564 |
| 3,344,186 | 9/1967 | Augstein et al. | 260/564 |
| 3,953,506 | 4/1976 | Spicer et al. | 260/553 A |
| 3,953,606 | 4/1976 | Spicer et al. | 424/322 |
| 4,005,140 | 1/1977 | Spicer et al. | 260/553 A |
| 4,041,070 | 8/1977 | Asato et al. | 260/553 A |
| 4,049,717 | 9/1977 | Asato | 260/575 |
| 4,051,183 | 9/1977 | Asato | 260/553 A |
| 4,062,856 | 12/1977 | Spicer et al. | 260/295.5 B |
| 4,072,711 | 2/1978 | Asato et al. | 260/554 |
| 4,076,952 | 2/1978 | Asato et al. | 560/28 |
| 4,088,786 | 5/1978 | Asato et al. | 424/322 |
| 4,089,976 | 5/1978 | Asato | 424/322 |
| 4,091,018 | 5/1978 | Asato | 260/562 R |
| 4,199,510 | 4/1980 | Zweig et al. | 260/326 S |
| 4,287,346 | 9/1981 | Tanaka et al. | 546/330 |
| 4,327,217 | 4/1982 | Tanaka et al. | 546/193 |
| 4,363,921 | 12/1982 | Tanaka et al. | 549/74 |
| 4,365,067 | 12/1982 | Fujimoto et al. | 541/342 |
| 4,396,764 | 8/1983 | Tanaka et al. | 544/124 |
| 4,405,644 | 9/1983 | Kabbe et al. | 424/322 |

FOREIGN PATENT DOCUMENTS

| | | | |
|---|---|---|---|
| 471281 | 2/1951 | Canada | 564/104 |
| 599722 | 3/1948 | United Kingdom . | |
| 800,869 | 9/1958 | United Kingdom . | |
| 842,322 | 7/1960 | United Kingdom . | |

OTHER PUBLICATIONS

Turner, R. W., *Synthesis*, 332 (1975).
Grigat, E., *Angew. Chem. Int. Ed.*, 11, 949 (1972).
Grigat et al, *Chem. Ber.*, 98, 2619 (1965).
Grigat et al, *Chem. Ber.*, 99, 958 (1966).
Grigat et al, *Angew Chem. Int. Ed.*, 6, 206 (1967).

*Primary Examiner*—Anton H. Sutto
*Attorney, Agent, or Firm*—Richard G. Waterman; Kenneth L. Loertscher; Ronald G. Brookins

[57] ABSTRACT

This invention relates to novel cyanoguanidine compounds and the intermediate N'-cyano-N-(1,2,3,4-tetrahydro-1-naphthyl)-S-methylisothiourea. These novel compounds are useful as animal growth promoting agents.

18 Claims, No Drawings

CYANOGUANIDINES USEFUL AS ANIMAL GROWTH PROMOTING AGENTS

SUMMARY OF THE INVENTION

This invention is directed to novel cyanoguanidine compounds of the formula:

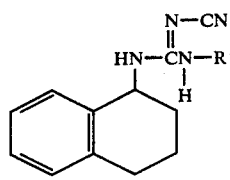
(I)

wherein R represents lower alkyl ($C_1$ to $C_3$, inclusive), or lower alkenyl ($C_3$).

This invention is also directed to the intermediate compound N'-cyano-N-(1,2,3,4-tetrahydro-1-naphthyl)-S-methylisothiourea represented by the following formula:

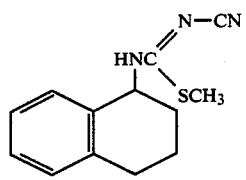
(II)

This intermediate is useful for producing the cyanoguanidine compounds of Formula I.

This invention is also directed to a method of promoting the growth of animals in need thereof which comprises administering an effective amount of at least one of the compounds of Formula I or Formula II to said animals.

This invention is also directed to animal feed compositions comprising at least one of the compounds of Formula I or Formula II in admixture with standard animal feed.

As used herein, the term "lower alkyl" refers to an alkyl group having from 1 to 3 carbon atoms such as methyl, ethyl, propyl, or isopropyl; the term "lower alkenyl" refers to an alkenyl group having 3 carbon atoms such as allyl; the term "animals" refers to those animals in which it is desirable to increase the growth rate and/or the feed conversion efficiency, such as poultry, swine, cattle or sheep; the term "effective amount" refers to that amount of compound or compounds sufficient to increase the growth rate and/or the feed conversion efficiency in animals without resulting in any significant adverse side effects.

DETAILED DESCRIPTION OF THE INVENTION

The novel cyanoguanidine compounds represented by Formula I and the intermediate, N'-cyano-N-(1,2,3,4-tetrahydro-1-naphthyl)-S-methylisothiourea represented by Formula II, can be prepared as follows:

The intermediate, N'-cyano-N-(1,2,3,4-tetrahydro-1-napthyl)-S-methylisothiourea, is prepared by contacting and mixing 1,2,3,4-tetrahydro-1-napthylamine and dimethyl cyanodithioiminocarbonate in the presence of a suitable organic solvent such as methanol, ethanol, propanol or acetonitrile under conditions at which the desired compound is formed. For example, the reaction proceeds at a temperature of between about 0° C. and 80° C. Typically, equimolar amounts of the reactants are employed, however the molar proportion of the reactants is not critical. The reaction is illustrated as follows:

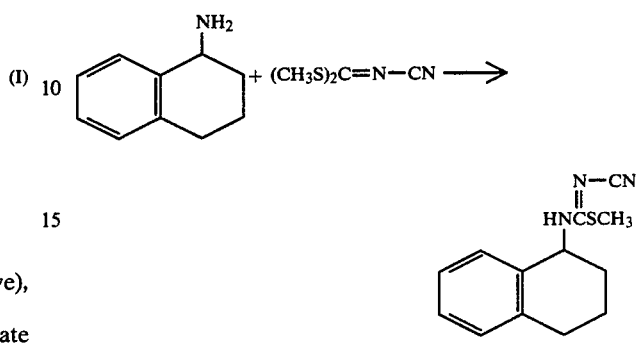

To prepare the alkyl and alkenyl substituted cyanoguanidine derivatives, N'-cyano-N-(1,2,3,4-tetrahydro-1-naphthyl)-S-methylisothiourea is reacted with an appropriate alkylamine or alkenylamine of the formula $H_2NR$ wherein R is lower alkyl or lower alkenyl in an appropriate solvent such as ethanol, acetonitrile, methanol, or propanol under conditions at which the desired compound is formed. For example, the reaction proceeds when the reaction mixture is heated at about 70° C. to 130° C. for about 8 hours to 2 weeks. The desired product can then be recovered using conventional procedures. The reaction can be illustrated as follows:

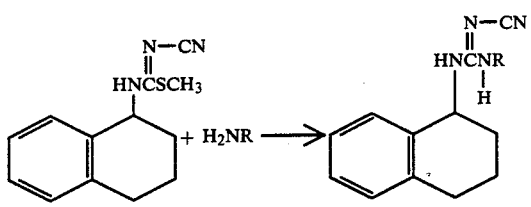

wherein R represents lower alkyl ($C_1$ to $C_3$, inclusive) or lower alkenyl ($C_3$).

One or more of the cyanoguanidines of this invention or the intermediate, N'-cyano-N-(1,2,3,4-tetrahydro-1-naphthyl)-S-methylisothiourea, can be administered in a growth promoting amount to an animal. The compounds of this invention can be administered to animals by conventional methods appreciated by one skilled in the art (for example, see the methods taught in U.S. Pat. Nos. 4,185,091; 4,209,518; and 4,333,923; incorporated herein by reference). When administered in the feed of an animal, usually about 1.3 to 90 milligrams of compound per kilogram of animal body weight per day is effective in promoting the growth of the animal. The exact amount of the compound or compounds to be employed will vary depending upon factors such as species of animal, or the size, weight, age, and health of the animal. In particular cases, the concentration to be administered may be determined by conventional dose titration techniques.

The present invention is further illustrated by the following examples; however, these examples should not be interpreted as a limitation upon the scope of the present invention.

EXAMPLE 1

Preparation of the intermediate, N'-cyano-N-(1,2,3,4-tetrahydro-1-napthyl)-S-methylisothiourea, represented by the formula:

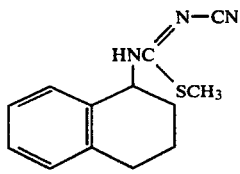

A solution of 73.6 grams (g) of 1,2,3,4-tetrahydro-1-naphthylamine in 75 milliliters (ml) of ethanol was slowly added to a solution of 73.1 g of dimethyl cyanodithioiminocarbonate in 200 ml of ethanol, keeping the temperature between 5° C. and 7° C. by means of an ice bath. After the addition was complete the reaction flask was kept in the ice bath for 30 minutes, removed from the ice bath and allowed to stand at room temperature for 3 hours during which time 103.5 g of N'-cyano-N-(1,2,3,4-tetrahydro-1-napthyl)-S-methylisothiourea precipitated as a white, crystalline solid, melting point (mp) 143°-144° C.

| Analysis | C | H | N |
|---|---|---|---|
| Calculated for C$_{13}$H$_{15}$N$_3$S: | 63.64 | 6.16 | 17.13 |
| Found: | 63.7 | 6.01 | 17.26 |

EXAMPLE 2

Preparation of N''-cyano-N-ethyl-N'-(1,2,3,4-tetrahydro-1-naphthyl)guanidine, represented by the formula:

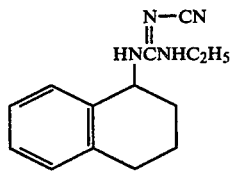

A solution of 6.13 g of N'-cyano-N-(1,2,3,4-tetrahydro-1-naphthyl)-S-methylisothiourea and 10 ml of 70% aqueous ethylamine in 90 ml of ethanol was heated at reflux with stirring for 20 hours. The reaction mixture was cooled in a refrigerator to give 2.44 g of N''-cyano-N-ethyl-N'-(1,2,3,4-tetrahydro-1-naphthyl)guanidine as a white, crystalline solid, mp 152°-153.5° C.

| Analysis | C | H | N |
|---|---|---|---|
| Calculated for C$_{14}$H$_{18}$N$_4$: | 69.39 | 7.49 | 23.12 |
| Found: | 69.5 | 7.54 | 23.18 |

EXAMPLE 3

Preparation of N''-cyano-N-isopropyl-N'-(1,2,3,4-tetrahydro-1-naphthyl)guanidine, represented by the following formula:

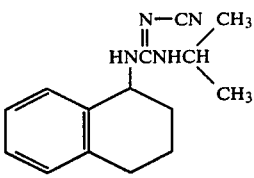

A solution of 30.0 g of N'-cyano-N-(1,2,3,4-tetrahydro-1-napthyl)-S-methylisothiourea and 40 ml of isopropylamine in 300 ml of acetonitrile was heated at reflux with stirring for 154 hours. The solvent and excess isopropylamine were removed by evaporation in vacuo, leaving the crude product as a tacky, white solid. Crystallization from isopropyl acetate followed by a recrystallization from a mixture of isopropyl acetate and 2-propanol gave 5.13 g of N''-cyano-N-isopropyl-N'-(1,2,3,4-tetrahydro-1-naphthyl)guanidine as a white, crystalline solid, mp 170.5°-172.5° C.

| Analysis | C | H | N |
|---|---|---|---|
| Calculated for C$_{15}$H$_{20}$N$_4$: | 70.28 | 7.86 | 21.86 |
| Found: | 70.2 | 7.70 | 21.76 |

EXAMPLE 4

Preparation of N''-cyano-N-n-propyl-N'-(1,2,3,4-tetrahydro-1-naphthyl)guanidine, represented by the following formula:

A solution of 12.3 g of N'-cyano-N-(1,2,3,4-tetrahydro-1-napthyl)-S-methylisothiourea and 16 ml of n-propylamine in 100 ml of acetonitrile was heated at reflux with stirring for 20 hours. The reaction mixture was then allowed to stand in a refrigerator to give 8.63 g of N''-cyano-N-n-propyl-N'-(1,2,3,4-tetrahydro-1-naphthyl)guanidine as a white, crystalline solid, mp 130.5°-131.5° C. A further quantity of the product was obtained by the concentration and subsequent cooling of the mother liquor.

| Analysis | C | H | N |
|---|---|---|---|
| Calculated for C$_{15}$H$_{20}$N$_4$: | 70.28 | 7.86 | 21.86 |
| Found: | 70.3 | 7.83 | 21.81 |

EXAMPLE 5

Preparation of N''-cyano-N-methyl-N'-(1,2,3,4-tetrahydro-1-naphthyl)guanidine, represented by the following formula:

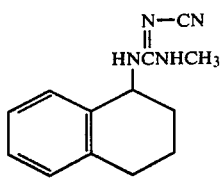

A solution of 12.3 g of N'-cyano-N-(1,2,3,4-tetrahydro-1-naphthyl)-S-methylisothiourea and 20 ml of 33% ethanolic methylamine in 200 ml of ethanol was heated at reflux with stirring for 22 hours. The solvent was then removed by evaporation in vacuo, leaving the crude product as a glassy, amorphous solid. Crystallization from a mixture of isopropyl acetate, methylcyclohexane and 2-propanol gave 7.03 g of N''-cyano-N-methyl-N'-(1,2,3,4-tetrahydro-1-naphthyl)guanidine as a white, crystalline solid, mp 169°–170° C.

| Analysis | C | H | N |
| --- | --- | --- | --- |
| Calculated for $C_{13}H_{16}N_4$: | 68.39 | 7.07 | 24.54 |
| Found: | 68.2 | 7.01 | 24.66 |

EXAMPLE 6

Preparation of N-allyl-N''-cyano-N'-(1,2,3,4-tetrahydro-1-napthyl)guanidine, represented by the following formula:

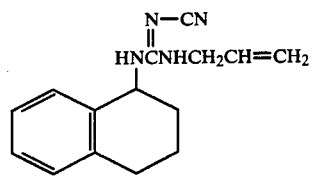

A solution of 24.5 g of N'-cyano-N-(1,2,3,4-tetrahydro-1-naphthyl)-S-methylisothiourea and 38 ml of allylamine in 400 ml of ethanol was heated at reflux for 87 hours. The solvent was removed from the reaction mixture by evaporation in vacuo, leaving a pale yellow semisolid which was crystallized from isopropyl acetate to give 11 g of N-allyl-N''-cyano-N'-(1,2,3,4-tetrahydro-1-naphthyl)guanidine as a white, crystalline solid, mp 130°–132° C.

| Analysis | C | H | N |
| --- | --- | --- | --- |
| Calculated for $C_{15}H_{18}N_4$: | 70.84 | 7.13 | 22.03 |
| Found: | 70.83 | 7.15 | 22.14 |

EXAMPLE 7

The animal growth promoting activity of the novel compounds of this invention was illustrated as follows:

CD-1 male mice from Charles River Breeding Laboratories, Portage, MI were received at about 3 weeks of age (14–16 grams). Upon arrival the mice were randomly assigned to groups of 16–20 and housed in plastic cages and acclimated on Purina Rodent Laboratory Chow No. 5002 ® (the stock diet) for three days. On the fourth day the mice were weighed and mice of the upper and lower weight extremes were discarded. The remaining mice were randomly assigned in groups of four to plastic cages. At this time, the stock diet was replaced with a 23% casein diet for the remaining 5 days of the acclimation period. Each cage of four mice was then randomly assigned either to a control group or a treatment group. Food and water were available ad libitum. Animals were housed in air conditioned rooms (72° F. to 76° F.) with automatically controlled lights (12 hours on, 12 hours off). During the treatment period the test mice in the control groups were fed the 23% casein diet and test mice in the treatment groups were fed the 23% casein diet mixed with the appropriate test compound. The concentration of all test compounds was 75 parts per million (ppm) in the 23% casein diet.

Each control and treatment group contained nine or ten cages of four mice (i.e., 36 or 40 mice per control or treatment group). The treatment period was nine days. During the first three days of the treatment period the mice were weighed daily and an average weight determined for each group (the initial average weight). The mice were again weighed daily during the last three days of the treatment period and an average weight determined (the final average weight). The final average weights and the initial average weights were used to calculate the average daily weight gains for the respective control and treatment groups. The percent weight gains were then calculated as shown in Table 1.

Composition of 23% casein diet:
Casein—23.0%
Dextrose—31.5%
Starch—31.5%
Corn oil—5.0%
Mineral Mix (AIN76)—3.5%
Vitamin Mix (AIN76A)—1.0%
Cellulose—4.0%
d,l-Methionine—0.3%
Choline Bitartrate—0.2%

TABLE 1

| Example Number | Compound | Dietary Level ppm | *Percent Weight Gain |
| --- | --- | --- | --- |
| 1 | N'—cyano-N—(1,2,3,4-tetrahydro-1-naphthyl-S—methylisothiourea | 75 | 106 |
| 2 | N''—cyano-N—ethyl-N'-(1,2,3,4-tetrahydro-1-naphthyl)-guanidine | 75 | 114 |
| 3 | N''—cyano-N—isopropyl-N'—(1,2,3,4-tetrahydro-1-naphtyl)guanidine | 75 | 120 |
| 4 | N''-cyano-N—n-propyl-N'—(1,2,3,4-tetrahydro-1-naphthyl)guanidine | 75 | 108 |
| 5 | N''—cyano-N—methyl-N'—(1,2,3,4-tetrahydro-1-naphthyl)-guanidine | 75 | 105 |
| 6 | N—allyl-N''—cyano-N'—(1,2,3,4-tetrahydro-1-naphthyl)-guanidine | 75 | 104 |

*Percent Weight Gain = $\frac{\text{average daily weight gain treated group}}{\text{average daily weight gain control group}} \times 100$ The compounds of this invention have demonstrated herbicidal activity in standard tests.

What is claimed is:

1. A method for promoting the growth of animals comprising administering to said animals an effective amount of at least one compound corresponding to the formula:

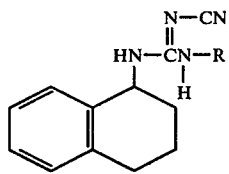

wherein R represents lower alkyl ($C_1$ to $C_3$, inclusive), or lower alkenyl ($C_3$).

2. The method of claim 1 wherein R represents ethyl.

3. The method of claim 1 wherein R represents isopropyl.

4. The method of claim 1 wherein R represents n-propyl.

5. The method of claim 1 wherein R represents methyl.

6. The method of claim 1 wherein R represents allyl.

7. A compound of the formula:

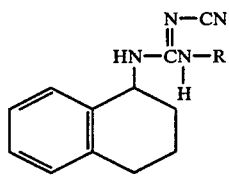

wherein R represents lower alkyl ($C_1$ to $C_3$, inclusive), or lower alkenyl ($C_3$).

8. The compound of claim 7 wherein R represents ethyl.

9. The compound of claim 7 wherein R represents isopropyl.

10. The compound of claim 7 wherein R represents n-propyl.

11. The compound of claim 7 wherein R represents methyl.

12. The compound of claim 7 wherein R represents allyl.

13. An animal feed composition suitable for promoting the growth of animals which comprises a mixture of animal feed and an effective amount of at least one compound corresponding to the formula:

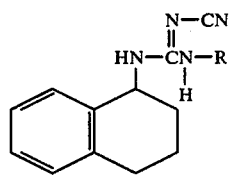

wherein R represents lower alkyl ($C_1$ to $C_3$, inclusive), or lower alkenyl ($C_3$).

14. The animal feed composition of claim 13 wherein R represents ethyl.

15. The animal feed composition of claim 13 wherein R represents isopropyl.

16. The animal feed composition of claim 13 wherein R represents n-propyl.

17. The animal feed composition of claim 13 wherein R represents methyl.

18. The animal feed composition of claim 13 wherein R represents allyl.

* * * * *